(12) United States Patent
Zhang et al.

(10) Patent No.: US 9,139,542 B2
(45) Date of Patent: Sep. 22, 2015

(54) CRYSTALLINE FORM OF A SUBSTITUTED THIAZOLYLACETIC ACID TRIETHYLAMINE SALT

(71) Applicants: Weijiang Zhang, Concord, CA (US); Michael R. Tracey, Charles City, IA (US); Junning Lee, El Granada, CA (US)

(72) Inventors: Weijiang Zhang, Concord, CA (US); Michael R. Tracey, Charles City, IA (US); Junning Lee, El Granada, CA (US)

(73) Assignee: THERAVANCE BIOPHARMA ANTIBIOTICS IP, LLC, South San Francisco, CA (US)

( * ) Notice: Subject to any disclaimer, the term of this patent is extended or adjusted under 35 U.S.C. 154(b) by 0 days.

(21) Appl. No.: 14/198,975

(22) Filed: Mar. 6, 2014

(65) Prior Publication Data

US 2014/0275554 A1 Sep. 18, 2014

Related U.S. Application Data

(60) Provisional application No. 61/779,091, filed on Mar. 13, 2013.

(51) Int. Cl.
*C07D 277/40* (2006.01)
*C07D 277/593* (2006.01)

(52) U.S. Cl.
CPC .......... *C07D 277/40* (2013.01); *C07D 277/593* (2013.01)

(58) Field of Classification Search
None
See application file for complete search history.

(56) References Cited

U.S. PATENT DOCUMENTS

| | | |
|---|---|---|
| 4,220,761 A | 9/1980 | Takaya et al. |
| 4,284,631 A | 8/1981 | Takaya et al. |
| 4,341,775 A | 7/1982 | Takaya et al. |
| 4,366,153 A | 12/1982 | Takaya et al. |
| 4,372,952 A | 2/1983 | Takaya et al. |
| 4,487,767 A | 12/1984 | Takaya et al. |
| 4,598,147 A | 7/1986 | Takaya et al. |
| 4,698,337 A | 10/1987 | Takaya et al. |
| 6,974,797 B2 | 12/2005 | Fatheree et al. |
| 7,341,993 B2 | 3/2008 | Fatheree et al. |
| 7,553,962 B2 | 6/2009 | Fatheree et al. |
| 7,601,690 B2 | 10/2009 | Fatheree et al. |
| 7,612,037 B2 | 11/2009 | Fatheree et al. |
| 7,649,080 B2 | 1/2010 | Fatheree et al. |
| 7,655,621 B2 | 2/2010 | Fatheree et al. |
| 7,713,931 B2 | 5/2010 | Fatheree et al. |
| 7,728,127 B2 | 6/2010 | Fatheree et al. |

FOREIGN PATENT DOCUMENTS

| | | |
|---|---|---|
| EP | 0249170 A2 | 12/1987 |
| EP | 0293771 A2 | 12/1988 |
| GB | 2033377 A | 5/1980 |
| WO | 03/031449 A2 | 4/2003 |
| WO | 03/040116 A1 | 5/2003 |
| WO | 03/099858 A1 | 12/2003 |
| WO | 2006/008160 A1 | 1/2006 |
| WO | 2006/104141 A1 | 10/2006 |

OTHER PUBLICATIONS

Long et al., "Exploring the positional attachment of glycopeptide/B-lactam heterodimers", J. Antibiotics, 61(10): 603-614 (2008).

*Primary Examiner* — Nyeemah A Grazier
(74) *Attorney, Agent, or Firm* — Jeffrey A. Hagenah

(57) ABSTRACT

The invention relates to a crystalline form of a triethylamine salt of (2Z)-2-(2-amino-5-chlorothiazol-4-yl)-2-(3-N-tert-butoxycarbonylaminopropoxyimino)acetic acid. The invention also relates to processes and intermediates for preparing the crystalline form. The crystalline form is useful as an intermediate for preparing cross-linked glycopeptide-cephalosporin antibiotics.

13 Claims, 3 Drawing Sheets

CRYSTALLINE FORM OF A SUBSTITUTED THIAZOLYLACETIC ACID TRIETHYLAMINE SALT

CROSS-REFERENCE TO RELATED APPLICATIONS

This application claims the benefit of U.S. Provisional Application No. 61/779,091, filed on Mar. 13, 2013; the entire disclosure of which is incorporated herein by reference in its entirety.

BACKGROUND OF THE INVENTION

1. Field of the Invention

The present invention relates to a novel crystalline form of a triethylamine salt of a substituted thiazolylacetic acid compound which is useful as an intermediate for preparing cross-linked glycopeptide-cephalosporin antibiotics. This invention also relates to processes and intermediates for preparing the crystalline form.

2. State of the Art

U.S. Pat. No. 6,974,797 B2 discloses a compound of the formula:

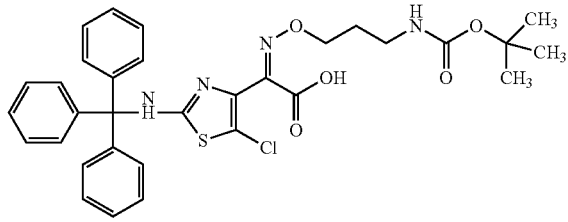 [SMILES: CC(C)(C)OC(=O)NCCCO/N=C(\C(=O)O)c1nc(NC(c2ccccc2)(c2ccccc2)c2ccccc2)sc1Cl]

This compound is a synthetic intermediate used in the preparation of a cross-linked glycopeptide-cephalosporin antibiotic. The compound is described as a tan solid which can be purified by extraction to remove residual succinimide (Example A, Step 4; Column 29, lines 07 to 37). This compound is not described as being crystalline.

Although this intermediate compound is useful for preparing cross-linked glycopeptide-cephalosporin antibiotics, it would be advantageous to provide an intermediate compound that is in crystalline form. Crystalline intermediates are advantageous because impurities are typically removed or substantially reduced during the crystallization process thereby resulting in an intermediate having improved purity. Moreover, crystalline materials often have improved storage stability and better handling properties compared to non-crystalline materials. Accordingly, it would be desirable to provide an intermediate useful for preparing cross-linked glycopeptide-cephalosporin antibiotics which is in crystalline form.

SUMMARY OF THE INVENTION

The present invention provides a crystalline form of (2Z)-2-(2-amino-5-chlorothiazol-4-yl)-2-(3-N-tert-butoxycarbonylaminopropoxyimino)acetic acid triethylamine salt.

(2Z)-2-(2-Amino-5-chlorothiazol-4-yl)-2-(3-N-tert-butoxycarbonylamino-propoxyimino)acetic acid is a compound having formula I:

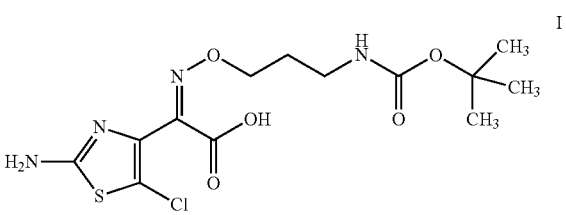 [SMILES: CC(C)(C)OC(=O)NCCCO/N=C(\C(=O)O)c1nc(N)sc1Cl]

This compound and its crystalline triethylamine salt are useful as intermediates for preparing cross-linked glycopeptide-cephalosporin antibiotics.

Accordingly, in one aspect, the present invention provides a crystalline form of (2Z)-2-(2-amino-5-chlorothiazol-4-yl)-2-(3-N-tert-butoxycarbonylaminopropoxyimino)-acetic acid triethylamine salt; wherein the crystalline form is characterized by at least one of several defined properties.

In one embodiment, the crystalline form is characterized by a powder x-ray diffraction pattern comprising diffraction peaks at 2θ values of 5.00±0.20, 12.92±0.20, 15.00±0.20, 16.92±0.20, 22.36±0.20, 23.36±0.20 and 24.54±0.20. In another embodiment, the crystalline form is further characterized by a powder x-ray diffraction pattern substantially in accordance with FIG. 1.

In another embodiment, the crystalline form is characterized by a melting onset temperature of about 139° C. In another embodiment, the crystalline form is further characterized by a differential scanning calorimetry trace substantially in accordance with FIG. 2.

In another embodiment, the crystalline form is characterized by crystalline parameters at 293 K comprising (i) a monoclinic crystal system, (ii) a P2$_1$/c space group, and (iii) unit cell dimensions substantially equal to: a=8.587(4) Å, b=35.594(12) Å, c=8.308(3) Å and β=100.63(4)° (as determined by single crystal X-ray crystallographic analysis).

In another aspect, the present invention is directed to (2Z)-2-(2-amino-5-chlorothiazol-4-yl)-2-(3-N-tert-butoxycarbonylaminopropoxyimino)acetic acid (i.e., the compound of formula I) or a salt thereof, which compound is useful both as an intermediate for preparing a crystalline triethylamine salt of this invention and as an intermediate for preparing cross-linked glycopeptide-cephalosporin antibiotics.

In another aspect, the present invention provides a process for preparing a crystalline form of (2Z)-2-(2-amino-5-chlorothiazol-4-yl)-2-(3-N-tert-butoxycarbonylaminopropoxyimino)acetic acid triethylamine salt. In one embodiment, the process comprises the steps of:

(a) reacting (2Z)-2-(2-aminothiazol-4-yl)-2-(3-N-tert-butoxycarbonylaminopropoxyimino)acetic acid or a salt thereof with a chlorinating agent to form (2Z)-2-(2-amino-5-chlorothiazol-4-yl)-2-(3-N-tert-butoxycarbonyl-aminopropoxyimino)acetic acid or a salt thereof; and (b) contacting (2Z)-2-(2-amino-5-chlorothiazol-4-yl)-2-(3-N-tert-butoxycarbonylaminopropoxyimino)acetic acid or a salt thereof with triethylamine to form a crystalline form of (2Z)-2-(2-amino-5-chlorothiazol-4-yl)-2-(3-N-tert-butoxycarbonylaminopropoxyimino)acetic acid triethylamine salt.

In another aspect, this invention provides a method of forming a crystalline form of (2Z)-2-(2-amino-5-chlorothiazol-4-yl)-2-(3-N-tert-butoxycarbonylamino-propoxyimino)acetic acid triethylamine salt. In one embodiment, the method comprises the steps of:

(a) providing a solution of (2Z)-2-(2-amino-5-chlorothiazol-4-yl)-2-(3-N-tert-butoxycarbonylaminopropoxyimino)acetic acid triethylamine salt in methanol; and (b) contacting the solution from step (a) with isopropyl acetate to form a crystalline form of (2Z)-2-(2-amino-5-chlorothiazol-4-yl)-2-(3-N-tert-butoxycarbonyl-aminopropoxyimino)acetic acid triethylamine salt.

Other aspects and embodiments of this invention are disclosed herein.

BRIEF DESCRIPTION OF THE DRAWINGS

Various aspects of the present invention are illustrated by reference to the accompanying drawings.

DETAILED DESCRIPTION OF THE INVENTION

Figure 1:
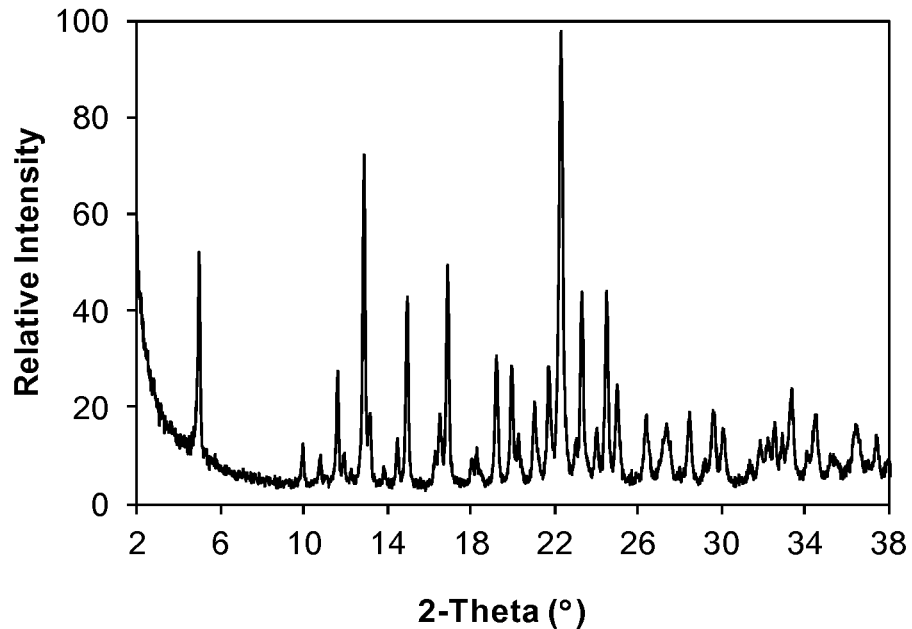
FIG. 1 shows a powder x-ray diffraction (PXRD) pattern for a crystalline form of (2Z)-2-(2-amino-5-chlorothiazol-4-yl)-2-(3-N-tert-butoxycarbonylaminopropoxyimino)-acetic acid triethylamine salt.

Amongst various aspects and embodiments, the present invention provides a crystalline form of (2Z)-2-(2-amino-5-chlorothiazol-4-yl)-2-(3-N-tert-butoxycarbonyl-aminopropoxyimino)acetic acid triethylamine salt, and processes and intermediates for preparing the crystalline form.

The crystalline form of this invention typically contains between about 0.90 and about 1.10 molar equivalents of triethylamine per molar equivalent of the compound of formula I; including between about 0.95 and about 1.05 molar equivalents of triethylamine per molar equivalent of the compound of formula I. In a particular embodiment, the triethylamine salt of this invention contains about 1 molar equivalent of triethylamine per molar equivalent of the compound of formula I. The molar ratio is determined using conventional methods, such as $^{13}C$ NMR, single crystal X-ray crystallographic analysis, elemental analysis, ion analysis or HPLC.

Methods for preparing the crystalline form of this invention are provided in the Examples. Typically, (2Z)-2-(2-amino-5-chlorothiazol-4-yl)-2-(3-N-tert-butoxycarbonylaminopropoxyimino)acetic acid or a salt thereof is contacted with an excess of triethylamine in a diluent. For example, the amount of triethylamine employed typically ranges from about 1.1 to about 5.0 molar equivalents; including about 2.0 to about 4.0 molar equivalents, such as about 4.0 molar equivalents per mole of the compound of formula I. Generally, this reaction is conducted at a temperature ranging from about −10° C. to about 10° C.; including about −5° C. to about 5° C., such as about 0° C. Suitable diluents for this reaction are those in which the triethylamine salt has limited solubility, such as acetonitrile, isopropyl acetate and the like. The crystalline triethylamine salt typically precipitates from solution and is collected by conventional means, such as filtration.

The crystalline triethylamine salt of this invention can also be formed or recrystallized by first forming a solution of (2Z)-2-(2-amino-5-chlorothiazol-4-yl)-2-(3-N-tert-butoxycarbonylaminopropoxyimino)acetic acid triethyl amine in methanol and then contacting the methanol solution with isopropyl acetate. Typically, the triethylamine salt in dissolved in about 2.5 mL/g to about 3.5 mL/g of methanol, such as about 3 mL/g. The methanol solution is then contacted with isopropyl acetate by either adding the methanol solution to isopropyl acetate or by adding isopropyl acetate to the methanol solution. Generally, the amount of isopropyl acetate employed ranges from about 5 mL to about 15 mL per gram of triethylamine salt, such as about 10 mL/g. This process is typically conducted at a temperature of about −10° C. to about 25° C., such as about 0° C., for about 1 to about 24 hours, or until the crystalline triethylamine salt has substantially precipitated from the diluent. The crystalline triethylamine salt is typically collected by conventional means, such as filtration. Surprisingly, when ethanol is used in place of methanol, a gummy material is formed that is not filterable.

The triethylamine employed in this invention is commercially-available, e.g., from Sigma-Aldrich, St. Louis, Mo.

The (2Z)-2-(2-amino-5-chlorothiazol-4-yl)-2-(3-N-tert-butoxycarbonylamino-propoxyimino)acetic acid employed in this invention can be readily prepared from commercially-available starting materials and reagents using the procedures described in the Examples.

For example, (2Z)-2-(2-amino-5-chlorothiazol-4-yl)-2-(3-N-tert-butoxycarbonylaminopropoxyimino)acetic acid can be prepared as shown in Scheme A:

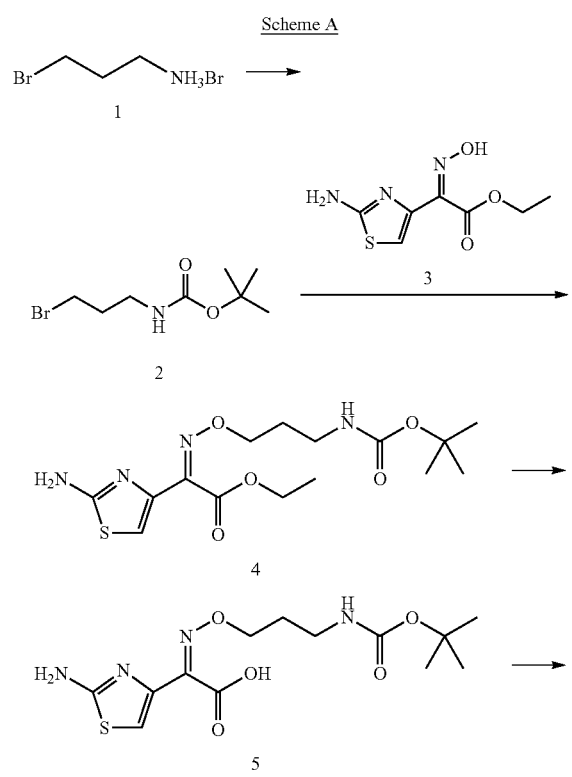

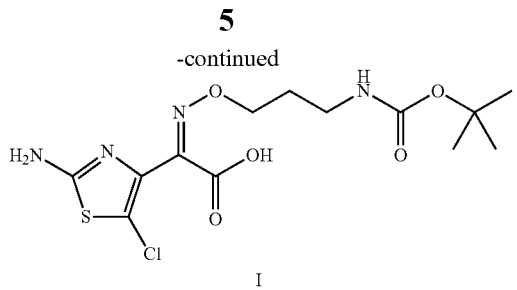

I

As shown in Scheme A, 3-bromopropylamine hydrobromide (1) is acylated to form tert-butyl 3-bromopropylcarbamate (2). This reaction is typically conducted by reacting 1 with about 0.9 to about 1.1 molar equivalents of di-tert-butyl dicarbonate in the presence of a base such as an alkali metal hydroxide, for example, sodium hydroxide, potassium hydroxide and the like. The reaction is generally conducted in a diluent at a temperature in the range of about 0° C. to about 20° C. for about 1 to about 6 hours, or until the reaction is substantially complete. In one embodiment, the reaction is conducted in a two-phase diluent, such as a mixture of heptane and water. The reaction product 2 can be isolated by conventional methods, such as extraction, filtration, crystallization or chromatography.

Compound 2 is then reacted with ethyl 2-amino-α-(hydroxyimino)-4-thiazoleacetate (3) to form ethyl (2Z)-2-(2-aminothiazol-4-yl)-2-(3-N-tert-butoxycarbonylaminopropoxyimino)acetate (4). This reaction is typically conducted by reacting 3 with about 1.1 to about 1.5 molar equivalents of 2 in the presence of a base such as an alkali metal carbonate, for example, potassium carbonate, sodium carbonate and the like. The reaction is generally conducted in a diluent at a temperature in the range of about 10° C. to about 40° C., such as 30° C., for about 6 to about 24 hours, or until the reaction is substantially complete. In one embodiment, the diluent is N,N-dimethylformamide (DMF) optionally containing water. The reaction product 4 can be isolated by conventional methods, such as extraction, filtration, crystallization or chromatography.

In one embodiment, compound (4) is purified by, for example, recrystallization to remove substantially all residual bromide anions from the product before conducting the next reaction. If residual bromide anions are not removed from (4), unwanted bromination products may occur during the subsequent chlorination reaction.

The ethyl 2-amino-α-(hydroxyimino)-4-thiazoleacetate (3) employed in this reaction is commercially-available from, for example, Sigma-Aldrich, St. Louis, Mo. 63103. If desired, other esters of 2-amino-α-(hydroxyimino)-4-thiazoleacetic acid may also be employed in this reaction, such as the methyl, n-propyl, isopropyl, n-butyl or benzyl ester and the like.

Compound 4 is then saponified to form (2Z)-2-(2-aminothiazol-4-yl)-2-(3-N-tert-butoxycarbonylaminopropoxyimino)acetic acid (5). This reaction is typically conducted by reacting 4 with about 1.1 to about 1.3 molar equivalents of an alkali metal hydroxide, such as sodium hydroxide, potassium hydroxide and the like. The reaction is generally conducted in a diluent at a temperature in the range of about 10° C. to about 40° C. for about 2 to about 24 hours, or until the reaction is substantially complete. In one embodiment, the diluent is a mixture of ethanol and water. The reaction product 5 or a salt thereof can be isolated by conventional methods, such as extraction, filtration, crystallization or chromatography.

Compound 5 or a salt thereof is then chlorinated to form (2Z)-2-(2-amino-5-chlorothiazol-4-yl)-2-(3-N-tert-butoxycarbonylaminopropoxyimino)acetic acid (compound of formula I). This reaction is typically conducted by reacting 5 with about 1.1 to about 1.4 molar equivalents of a chlorinating agent, such as N-chlorosuccinimide, N-chlorophthalimide, N-chlorosaccharine and the like. The reaction is generally conducted in a diluent at a temperature in the range of about 10° C. to about 30° C. for about 1 to about 6 hours, or until the reaction is substantially complete. In one embodiment, the diluent is ethyl acetate optionally containing methanol, such as a 90:10 v/v mixture of ethyl acetate and methanol. If the chlorinating agent is not soluble in the reaction mixture, the reaction mixture is typically stirred vigorously to contact the reactants. In one embodiment, to promote the reaction of the chlorinating agent with 5, half of the requisite amount of ethyl acetate is added to a solution of 5 in methanol, followed by the chlorinating agent (such as N-chlorosuccinimide) and then the remaining amount of ethyl acetate is added. The compound of formula I can be isolated by conventional methods, such as extraction, filtration, crystallization or chromatography.

EXAMPLES

The following examples are provided to illustrate various representative embodiments and aspects of this invention and are not intended to limit the scope of this invention unless specifically indicated.

All reagents, starting materials and solvents used in the following examples were purchased from commercial suppliers (such as Sigma-Aldrich Chemical Company, St. Louis, Mo.) and were used without further purification unless otherwise indicated. The following abbreviations are used for diluents: DCM=dichloromethane; DMF=N,N-dimethylformamide; DMSO=dimethyl sulfoxide; EtOAc=ethyl acetate; MeOH=methanol; and THF=tetrahydrofuran.

$^1$H NMR spectra were recorded on a 400 MHz Varian AS400 spectrometer, unless otherwise indicated. Chemical shifts are reported as δ values in ppm relative to tetramethylsilane (TMS) as an internal standard. Coupling constants (J values) are given in hertz (Hz) and multiplicities are reported using the following abbreviations: s=singlet, d=doublet, t=triplet, q=quartet, m=multiplet, br=broad, nd=not determined Example 1

Preparation of Tert-Butyl 3-Bromopropylcarbamate

To a solution of sodium hydroxide (105 g, 2.625 mol) in water (1.15 L) maintained at a temperature at or slightly below 10° C. was added a solution of di-tert-butyl dicarbonate (229 g, 1.05 mol) in heptane (1.03 L). The flask containing the solution of di-tert-butyl dicarbonate was rinsed with heptane (125 mL) and the rinsate was added to the reaction mixture. The resulting mixture was cooled to a temperature at or slightly below 10° C. and a solution of 3-bromopropylamine hydrobromide (251 g, 1.15 mol) in water (250 mL) was added dropwise at a rate that allowed the internal reaction temperature to be maintained below about 20° C. The flask containing the solution of 3-bromopropylamine hydrobromide was rinsed with water (20 mL) and the rinsate was added to the reaction mixture. After the addition was complete, the reaction mixture was allowed to slowly warm to room temperature (about 22° C.) and stirring was continued for about 2 hours at room temperature. The stirring was discontinued and the mixture was allowed to stand for 30 minutes. The lower aqueous layer was separated from the organic layer and discarded. To the organic layer was added a saturated aqueous sodium chloride solution (250 mL) and the resulting mixture was stirred for 5 min. The mixture was allowed to stand for 30 minutes and the lower aqueous layer was separated and discarded. The organic layer was concentrated to a volume of about 350 mL and this concentrated solution was cooled to 5° C. and stirred for 4 hours at 5° C. The resulting precipitate was collected by vacuum filtration to provide the title compound as a white crystalline solid (211 g, 84% yield). The filtrate was concentrated and the concentrated solution was cooled to 5° C. and stirred for 4 hours at 5° C. The resulting additional precipitate was collected by vacuum filtration to provide an additional amount of the title compound (17 g, 6.8% yield). $^1$H NMR (400 MHz, DMSO-$d_6$) δ $^1$H NMR (400 MHz, DMSO-$d_6$) δ 3.50 (t, J=6.8 Hz, 2H), 3.03 (q, J=6.8 Hz, 2H), 1.91 (m, J=6.8 Hz, 2H), 1.38 (s, 9H).

Example 2

Preparation of Ethyl (2Z)-2-(2-Aminothiazol-4-yl)-2-(3-N-tert -butoxycarbonylaminopropoxyimino) acetate To a mixture of ethyl 2-amino-α-(hydroxyimino)-4-thiazoleacetate (139.9 g, 650 mmol), tert-butyl 3-bromopropylcarbamate (209.0 g, 877 5 mmol) and powdered potassium carbonate (157.2 g, 1137.5 mmol) was added DMF (550 mL) and water (24.4 mL). The resulting mixture was stirred at 30° C. for about 11 hours. The reaction mixture was cooled to room temperature and ethyl acetate (2.3 L) and water (1.7 L) were added and the resulting mixture was stirred for 5 min. The mixture was allowed to stand for 60 min. and the lower layer (aqueous layer) was separated and discarded. An aqueous sodium bicarbonate solution (10 wt. %, 600 mL) was added and the resulting mixture was stirred for 5 min. The mixture was allowed to stand for 60 min. and the lower layer (aqueous layer) was separated and discarded. An aqueous sodium chloride solution (10 wt. %, 600 mL) was added and the resulting mixture was stirred for 5 min. The mixture was allowed to stand for 60 min. and the lower layer (aqueous layer) was separated and discarded. The organic layer was concentrated to a volume of about 600 mL. Hexanes (250 mL) were added dropwise to the concentrate with gently stirring at 0° C. for 1 hour to form a precipitate. The precipitate was collected by vacuum filtration to give the title compound (232 g, 96% yield) as an off-white crystalline solid. $^1$H NMR (400 MHz, DMSO-$d_6$) δ 7.25 (s, 2H), 6.89 (s, 1H), 6.82 (brs, 1H), 4.26 (q, J=8 Hz, 2H), 4.08 (t, J=6.4 Hz, 2H), 2.97 (q, J=6.4 Hz, 2H), 1.72 (m, J=6.4 Hz, 2H), 1.37 (s, 9H), 1.26 (t, J=8 Hz, 3H).

If desired, the product can be recrystallized. The crude material from several batches (1.0 kg, 91.2% purity) was dissolved in ethyl acetate (2 L) at 60° C. and heptane (1 L) was added slowly. The resulting solution was heated to 60° C. for 1 hour with stirring during which time a precipitate formed. The mixture was then allowed to cool slowly to room temperature. The precipitate was collected by vacuum filtration under dry nitrogen, washed with a mixture of heptane and EtOAc (1 L, 3:1) and dried under vacuum overnight to give the title compound (770 g, 98.3% purity).

Example 3

Preparation of (2Z)-2-(2-Aminothiazol-4-yl)-2-(3-N-tert -butoxycarbonylaminopropoxyimino)acetic Acid To a solution of ethyl (2Z)-2-(2-aminothiazol-4-yl)-2-(3-N-tert-butoxycarbonylaminopropoxyimino)acetate (232.0 g, 622 9 mmol) in absolute ethanol (1.63 L) was added dropwise a solution of sodium hydroxide (29.9 g, 747.4 mmol) in water (748 mL). The resulting mixture was heated at 35° C. for about 8 hours. The mixture was then cooled to about −5° C. and trifluoroacetic acid (about 10 mL) was added dropwise until the pH of the mixture was about 6.0. The mixture was then concentrated under vacuum to remove most of the volatile components and absolute ethanol (500 mL) was added. The resulting mixture was concentrated again to remove water via an azeotrope. This procedure was repeated again by adding absolute ethanol (500 mL) followed by concentrating to give the title compound which was used in the next reaction without any further isolation or purification.

Example 4

Preparation of (2Z)-2-(2-Amino-5-chlorothiazol-4-yl)-2-(3-N-tert -butoxycarbonylaminopropoxyimino) acetic Acid Triethylamine Salt Ethyl acetate (2.0 L) was added to a mixture of (2Z)-2-(2-aminothiazol-4-yl)-2-(3-N-tert-butoxycarbonylaminopropoxyimino)acetic acid (about 213 g, 627 mmol) in methanol (200 mL) to form a slurry. N-Chlorosuccinimide (108.0 g, 815 mmol) was added and the resulting mixture was stirred at room temperature for 3 hours. Water (2.5 L), sodium chloride (514 g) and trifluoroacetic acid (93 mL, 1254 mmol) were added and the resulting mixture was stirred for 15 min. The mixture was allowed to stand for 1 hour and then the lower aqueous layer was separated and discarded. The organic layer was concentrated under vacuum to a volume of about 500 mL. Acetonitrile (1.0 L) was added and the mixture was concentrated under vacuum. This was repeated by again adding acetonitrile (1.0 L) and concentrating the mixture under vacuum to a volume of about 600 mL. The mixture was then filtered through diatomaceous earth (Celite). Triethylamine (350 mL, 2508 mmol) was added and the mixture was cooled to 0° C. at which time a precipitate formed. The precipitate was collected by vacuum filtration, rinsed with acetonitrile (165 mL), and dried at room temperature under vacuum to give the title compound (224 g, 79% yield) as a light brown crystalline solid. $^1$H NMR (400 MHz, MeOH-$d_4$) δ 4.15 (t, J=6.4 Hz, 2H), 3.18 (m, 8H), 1.86 (m, 2H), 1.43 (s, 9H), 1.30 (t, J=7.9 Hz, 9H).

A similar procedure using ethanol in place of methanol resulted in a gummy product that was not filterable.

Example 5

Recrystallization of (2Z)-2-(2-Amino-5-chlorothiazol-4-yl)-2-(3-N-tert -butoxycarbonylaminopropoxyimino)acetic Acid Triethylamine Salt (2Z)-2-(2-Amino-5-chlorothiazol-4-yl)-2-(3-N-tert-butoxycarbonylamino-propoxyimino)acetic acid triethylamine salt (100.0 g) is dissolved in methanol (300 mL) and isopropyl acetate (3.0 L) is added dropwise. The resulting mixture is cooled overnight at 0° C. and then the precipitate is collected by vacuum filtration under a dry nitrogen atmosphere. The precipitate is rinsed with isopropyl acetate (600 mL; cooled to 0° C.) and then dried in a vacuum overnight to give the title compound as a crystalline solid.

Example 6

Powder X-Ray Diffraction

Powder X-ray diffraction analysis was performed using a Thermo ARL X'TRA X-ray diffractometer. The X-ray source was Cu—Kα radiation (λ=1.54051 Å) with output voltage of 40 kV and current of 45 mA. The instrument was operated in Bragg-Brentano geometry with incident, divergence, and scattering slits set to maximize the intensity at the sample. For measurement, a small amount of powder (5-25 mg) was gently pressed onto the sample holder to form a smooth surface and subjected to X-ray exposure. The samples were scanned in 2θ-2θ mode from 2° to 40° in 2θ with a step size of 0.02° and a scan speed corresponding to 1 sec exposure at each step. The data acquisition was controlled by Thermo ARL Measurement software (Version 1.2.0.0) and analyzed by Jade software (version 7.5.1).

A representative raw unprocessed PXRD pattern is shown in FIG. 1. Observed PXRD two-theta peak positions and d-spacings are shown in Table 1 (only peaks having a relative peak height (H %) of about 10% or greater are listed). With regard to the data, those skilled in the art will recognize that Bragg-Brentano geometry is prone to preferred orientation and it is possible that the relative intensities of the diffraction peaks may not represent the true relative intensities that would be obtained from an idealized distribution of spherical particles or from a diffraction pattern simulated from a single crystal data. It is also possible that some peaks are not seen in some diffraction patterns due to the extensive preferred orientation.

TABLE 1

PXRD Data

| Peak No. | 2-Theta | d(Å) | Height[1] | H %[2] |
|---|---|---|---|---|
| 1 | 5.00 | 17.65 | 605 | 45.7 |
| 2 | 11.66 | 7.59 | 332 | 25.1 |
| 3 | 12.92 | 6.85 | 980 | 74.1 |
| 4 | 13.20 | 6.70 | 210 | 15.9 |
| 5 | 14.52 | 6.10 | 141 | 10.7 |
| 6 | 15.00 | 5.90 | 565 | 42.8 |
| 7 | 16.56 | 5.35 | 213 | 16.1 |
| 8 | 16.92 | 5.24 | 653 | 49.4 |
| 9 | 19.26 | 4.61 | 375 | 28.4 |
| 10 | 19.98 | 4.44 | 341 | 25.8 |
| 11 | 20.32 | 4.37 | 133 | 10.1 |
| 12 | 21.08 | 4.21 | 223 | 16.9 |
| 13 | 21.76 | 4.08 | 322 | 24.3 |
| 14 | 22.36 | 3.97 | 1323 | 100.0 |
| 15 | 23.36 | 3.81 | 541 | 40.9 |
| 16 | 24.08 | 3.69 | 133 | 10.1 |
| 17 | 24.54 | 3.62 | 558 | 42.2 |
| 18 | 25.04 | 3.55 | 263 | 19.9 |
| 19 | 26.46 | 3.37 | 185 | 14.0 |
| 20 | 27.42 | 3.25 | 163 | 12.3 |
| 21 | 28.52 | 3.13 | 206 | 15.6 |
| 22 | 29.64 | 3.01 | 218 | 16.4 |
| 23 | 30.10 | 2.97 | 154 | 11.7 |
| 24 | 36.48 | 2.46 | 146 | 11.0 |

[1]Peak height from base line.
[2]Percent peak height compared to highest peak.

Example 7

Differential Scanning Calorimetry

Figure 2:
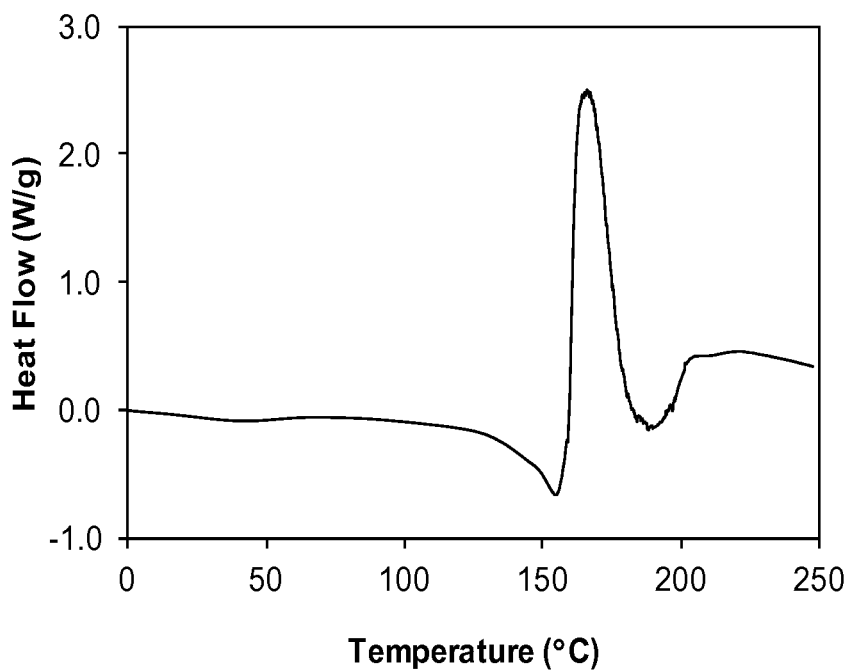
FIG. 2 shows a differential scanning calorimetry (DSC) trace for a crystalline form of (2Z)-2-(2-amino-5-chlorothiazol-4-yl)-2-(3-N-tert-butoxycarbonylaminopropoxy-imino) acetic acid triethylamine salt.

Differential scanning calorimetry (DSC) was performed using a TA Instruments Model Q-100 module with a Thermal Analyst controller. Data were collected and analyzed using TA Instruments Thermal Solutions software. A sample of crystalline (2Z)-2-(2-amino-5-chlorothiazol-4-yl)-2-(3-N-tert-butoxycarbonylaminopropoxyimino)acetic acid triethylamine salt (about 2 mg) was accurately weighed into an aluminum pan with lid. The sample was evaluated using a linear heating ramp of 10° C./min from ambient temperature to approximately 250° C. The DSC cell was purged with dry nitrogen during use. A representative DSC trace is shown in FIG. 2.

The DSC trace shows that the crystalline form had a melting onset at about 139° C.; however, the peak melting temperature could not be determined because the decomposition exotherm overlapped with the melting endotherm. There is a shallow endotherm in the range of from about 10° C. to about 60° C. which may correspond to the loss of surface adsorbed solvent or water. Additionally, melting was followed by a significant decomposition endotherm.

Example 8

Thermogravimetric Analysis

Figure 3:
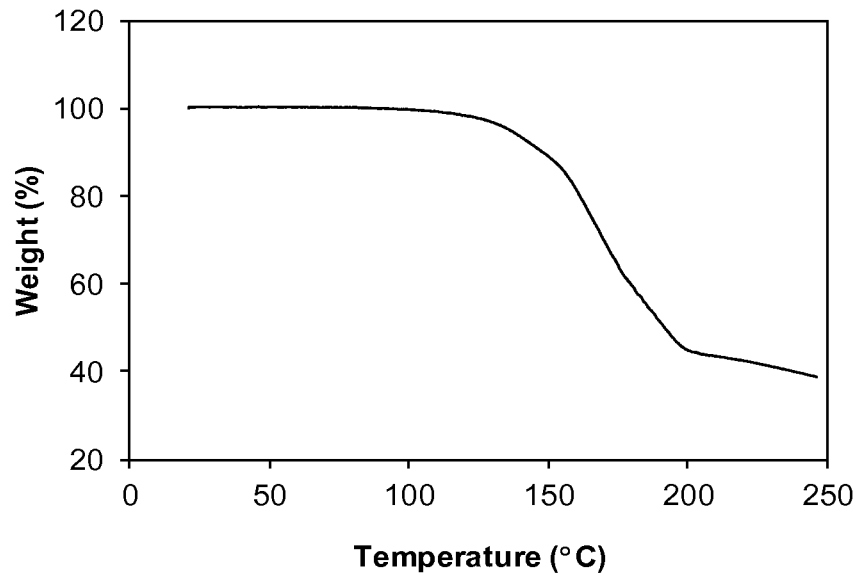
FIG. 3 shows a thermal gravimetric analysis (TGA) trace for a crystalline form of (2Z)-2-(2-amino-5-chlorothiazol-4-yl)-2-(3-N-tert-butoxycarbonylaminopropoxyimino)-acetic acid triethylamine salt.

Thermogravimetric analysis (TGA) was performed using a TA Instruments Model Q-500 module equipped with high resolution capability. Data were collected and analyzed using TA Instruments Thermal Solutions software. A sample of crystalline (2Z)-2-(2-amino-5-chlorothiazol-4-yl)-2-(3-N-tert-butoxycarbonylaminopropoxyimino)acetic acid triethylamine salt (about 10 mg) was placed onto a platinum pan and scanned with a high resolution-heating rate from ambient temperature to 300° C. The balance and furnace chambers were purged with nitrogen flows during use. A representative TGA trace is shown in FIG. 3.

The TGA trace shows that there was negligible weight loss (less than 0.25%) in the temperature range of from 20° C. to 120° C., which indicates that the sample was essentially anhydrous and not a solvate. Above 120° C., the sample lost about 50% of its weight which is likely due to post-melting evaporation of triethylamine and decomposition of the sample.

Example 9

Dynamic Moisture Sorption Assessment

Figure 4:
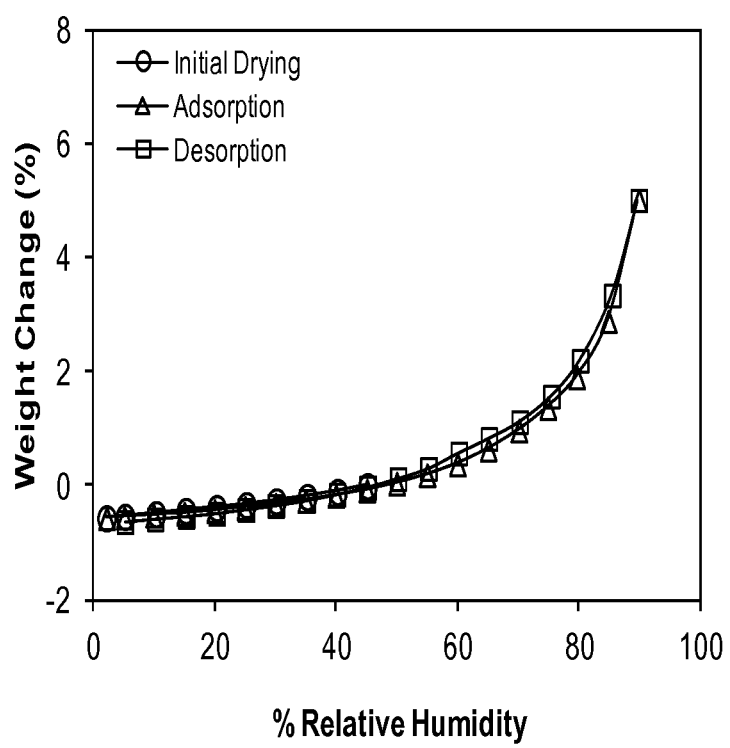
FIG. 4 shows a dynamic moisture sorption (DMS) trace for a crystalline form of (2Z)-2-(2-amino-5-chlorothiazol-4-yl)-2-(3-N-tert-butoxycarbonylaminopropoxyimino)-acetic acid triethylamine salt.
Figure 5:
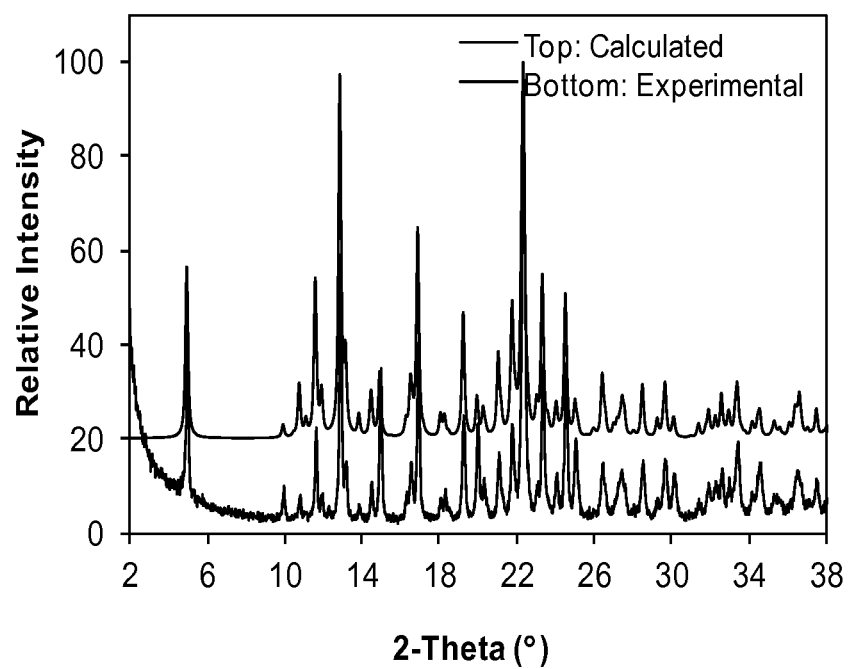
FIG. 5 shows a comparison of a powder x-ray diffraction (PXRD) pattern for a crystalline form of (2Z)-2-(2-amino-5-chlorothiazol-4-yl)-2-(3-N-tert-butoxycarbonylaminopropoxyimino)acetic acid triethylamine salt with a PXRD pattern calculated from single crystal x-ray data.

A dynamic moisture sorption (DMS) assessment (also known as a moisture sorption-desorption profile) was performed using a VTI atmospheric microbalance, SGA-100 system (VTI Corp., Hialeah, Fla. 33016). A sample of crystalline (2Z)-2-(2-amino-5-chlorothiazol-4-yl)-2-(3-N-tert-butoxycarbonylaminopropoxyimino)acetic acid triethylamine salt (about 10 mg) was used and the humidity was set at the ambient value at the start of the analysis. A typical DMS analysis consisted of three scans: ambient to 5% relative humidity (RH), 5% RH to 90% RH, 90% RH to 5% RH at a scan rate of 5% RH/step. The mass was measured every two minutes and the RH was changed to the next value (+/−5% RH) when the mass of the sample was stable to within 0.01% for 5 consecutive points. A representative DMS trace is shown in FIG. 4.

The DMS trace shows that initial drying of the crystalline form produced an insignificant moisture loss of 0.56% by weight. The crystalline form had an insignificant weight gain (moisture sorption) in the humidity range of 5% RH to 60% RH and then a weight gain of about 5.56% in the humidity range of 60% RH to 90% RH. The reversible moisture sorption/desorption profile demonstrates that the crystalline form has acceptable hygroscopicity and that it does not show hysteresis.

Example 10

Single Crystal X-Ray Analysis

The single crystal measurements were performed on a Nonius Kappa-CCD diffractometer equipped with Oxford Cryostream Liquid Nitrogen Cooler using Mo Kα radiation. The data were collected at 293 K and 120 K; the unit cell parameters given below are taken from 293 K data. The structure remained the same in this temperature range. The full sphere data were collected up to θ=26° (14370 reflections) at 120 K and θ=20° at 293 K (2148 reflections), respectively. Data reduction was performed using HKL Scalepack and cell parameters were obtained using Denzo and Scalepak from 7446 reflections within θ range 1 to 26°. The structure was solved using direct methods by SHELXS-97. The structure was refined by least square full matrix refinement using SHELXL97. All H-atoms connected to C-atoms were implemented from geometry and not refined, the others H-atoms were found on the Fourier difference map and refined isotropically.

The following unit cell parameters were determined at 293 K:
(i) a monoclinic crystal system,
(ii) a P2$_1$/c space group, and
(iii) unit cell dimensions substantially equal to: a=8.587(4) Å, b=35.594(12) Å, c=8.308(3) Å and β=100.63(4)°.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A crystalline form of (2Z)-2-(2-amino-5-chlorothiazol-4-yl)-2-(3-N-tert-butoxycarbonylaminopropoxyimino)acetic acid triethylamine salt; wherein the crystalline form is characterized by at least one of the following properties:
   (a) a powder x-ray diffraction pattern comprising diffraction peaks at 2θ values of 5.00±0.20, 12.92±0.20, 15.00±0.20, 16.92±0.20, 22.36±0.20, 23.36±0.20 and 24.54±0.20;
   (b) a melting onset temperature of about 139° C.; or
   (c) crystalline parameters at 293 K comprising (i) a monoclinic crystal system, (ii) a P2$_1$/c space group, and (iii) unit cell dimensions substantially equal to: a=8.587(4) Å, b=35.594(12) Å, c=8.308(3) Å and β=100.63(4)°.

2. The crystalline form of claim 1, wherein the crystalline form is characterized by a powder x-ray diffraction pattern comprising diffraction peaks at 2θ values of 5.00±0.20, 12.92±0.20, 15.00±0.20, 16.92±0.20, 22.36±0.20, 23.36±0.20 and 24.54±0.20.

3. The crystalline form of claim 2, wherein the crystalline form is further characterized by a powder x-ray diffraction pattern in which the peak positions are substantially in accordance with the peak positions shown in FIG. 1.

4. The crystalline form of claim 1, wherein the crystalline form is characterized by a melting onset temperature of about 139° C.

5. The crystalline form of claim 4, wherein the crystalline form is further characterized by a differential scanning calorimetry trace substantially in accordance with FIG. 2.

6. The crystalline form of claim 1, wherein the crystalline form is characterized by crystalline parameters at 293 K comprising (i) a monoclinic crystal system, (ii) a P2$_1$/c space group, and (iii) unit cell dimensions substantially equal to:
a=8.587(4) Å, b=35.594(12) Å, c=8.308(3) Å and β=100.63(4)°.

7. A process for preparing a crystalline form of (2Z)-2-(2-amino-5-chlorothiazol-4-yl)-2-(3-N-tert-butoxycarbonylaminopropoxyimino)acetic acid triethylamine salt according to claim 1, the process comprising the steps of:
   (a) reacting (2Z)-2-(2-aminothiazol-4-yl)-2-(3-N-tert-butoxycarbonylaminopropoxyimino)acetic acid or a salt thereof with a chlorinating agent to form (2Z)-2-(2-amino-5-chlorothiazol-4-yl)-2-(3-N-tert-butoxycarbonyl-aminopropoxyimino)acetic acid or a salt thereof; and
   (b) contacting (2Z)-2-(2-amino-5-chlorothiazol-4-yl)-2-(3-N-tert-butoxycarbonylaminopropoxyimino)acetic acid or a salt thereof with triethylamine to form a crystalline form of (2Z)-2-(2-amino-5-chlorothiazol-4-yl)-2-(3-N-tert-butoxycarbonylaminopropoxyimino)acetic acid triethylamine salt.

8. The process of claim 7, wherein the chlorinating agent is N-chlorosuccinimide.

9. The process of claim 7, wherein step (a) is conducted in a diluent comprising ethyl acetate.

10. The process of claim 9, wherein the diluent is a 90:10 v/v mixture of ethyl acetate and methanol.

11. The process of claim 7, wherein step (b) is conducted in a diluent comprising acetonitrile.

12. The process of claim 7, wherein in step (b), (2Z)-2-(2-amino-5-chlorothiazol-4-yl)-2-(3-N-tert-butoxycarbonylaminopropoxyimino)acetic acid or a salt thereof is contacted with about 1.1 to about 5.0 molar equivalents with triethylamine.

13. A method of forming a crystalline form of (2Z)-2-(2-amino-5-chlorothiazol-4-yl)-2-(3-N-tert-butoxycarbonylaminopropoxyimino)acetic acid triethylamine salt according to claim 1, the method comprising the steps of:
   (a) providing a solution of (2Z)-2-(2-amino-5-chlorothiazol-4-yl)-2-(3-N-tert-butoxycarbonylaminopropoxyimino)acetic acid triethylamine salt in methanol; and
   (b) contacting the solution from step (a) with isopropyl acetate to form a crystalline form of (2Z)-2-(2-amino-5-chlorothiazol-4-yl)-2-(3-N-tert-butoxycarbonyl-aminopropoxyimino)acetic acid triethylamine salt.

* * * * *